(12) United States Patent
Bruner et al.

(10) Patent No.: US 11,571,306 B2
(45) Date of Patent: Feb. 7, 2023

(54) DELIVERY SYSTEM WITH INTEGRATED CENTRAL RESTRAINT FOR AN IMPLANTABLE CARDIAC DEVICE

(71) Applicant: Boston Scientific Scimed, Inc., Maple Grove, MN (US)

(72) Inventors: Kenny Dwight Bruner, Windsor, CA (US); Padraig J. Savage, Santa Rosa, CA (US); Matthew Rust, Windsor, CA (US); Christopher Lashinski, Windsor, CA (US); Nathan D. Brown, Santa Rosa, CA (US); Michael J. Lee, Santa Rosa, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 32 days.

(21) Appl. No.: 16/658,252

(22) Filed: Oct. 21, 2019

(65) Prior Publication Data

US 2020/0121461 A1    Apr. 23, 2020

Related U.S. Application Data

(60) Provisional application No. 62/749,039, filed on Oct. 22, 2018.

(51) Int. Cl.
*A61F 2/24* (2006.01)

(52) U.S. Cl.
CPC .......... *A61F 2/2466* (2013.01); *A61F 2/2445* (2013.01); *A61F 2220/0008* (2013.01);
(Continued)

(58) Field of Classification Search
CPC .... A61F 2/2466; A61F 2/2427; A61F 2/2436; A61F 2/2445; A61F 2/24; A61F 2/2409;
(Continued)

(56) References Cited

U.S. PATENT DOCUMENTS 9,220,620 B2 * 12/2015 Hadley .................. A61F 2/966
2013/0131775 A1    5/2013 Hadley et al.
(Continued)

OTHER PUBLICATIONS

International Search Report and Written Opinion for the International Patent Application No. PCT/US2019/057124, dated Apr. 7, 2020, 14 pages.

*Primary Examiner* — Jennifer Dieterle
*Assistant Examiner* — Rebecca Lynee Zimmerman
(74) *Attorney, Agent, or Firm* — Seager, Tufte & Wickhem LLP

(57) ABSTRACT

Features for a restraint to facilitate delivery and deployment of an implantable cardiac device are described. The restraint may include a series of circumferential engagements for securing inwardly corresponding portions of the implant. The restraint may be located inside the implant and provide a radially inward force on the implant. The restraint may include a center shaft having a series of grooves configured to cooperate with corresponding splines of the implant. Distal or proximal advance of the restraint disengages the restraint from the implant. The implant may include a tubular frame configured to contract and be secured by the restraint in a contracted configuration and to expand upon disengagement from the restraint. The restraint may provide for a smaller overall cross-sectional profile of a transcatheter delivery system, for instance by negating the need for a distal delivery sheath.

20 Claims, 8 Drawing Sheets

(52) U.S. Cl.
CPC ............... *A61F 2220/0033* (2013.01); *A61F 2230/0056* (2013.01); *A61F 2230/0065* (2013.01)

(58) Field of Classification Search
CPC ...... A61F 2/2418; A61F 2/2442; A61F 2/246; A61F 2/2448; A61F 2002/9505; A61F 2/9517; A61F 2/9522; A61F 2/95; A61F 2002/9665; A61F 2/962
See application file for complete search history.

(56) References Cited

U.S. PATENT DOCUMENTS

| | | |
|---|---|---|
| 2014/0135907 A1 | 5/2014 | Gallagher et al. |
| 2014/0180383 A1* | 6/2014 | Loganathan .............. A61F 2/95 623/1.11 |

\* cited by examiner

DELIVERY SYSTEM WITH INTEGRATED CENTRAL RESTRAINT FOR AN IMPLANTABLE CARDIAC DEVICE

CROSS REFERENCE TO RELATED APPLICATIONS

This application is a non-provisional application of, and claims the benefit of priority to, U.S. Provisional Application Ser. No. 62/749,039, filed Oct. 22, 2018, entitled "DELIVERY SYSTEM WITH INTEGRATED CENTRAL RESTRAINT FOR AN IMPLANTABLE CARDIAC DEVICE" the entirety of which application is expressly incorporated by reference herein.

FIELD

The technology generally relates to implantable coronary medical devices. In particular, features are described for an apparatus to restrain an implant that reduces the cross-section profile of a delivery system to enable among other things the atraumatic delivery of a medical implant through its delivery system, its lumens, and the patient anatomy.

BACKGROUND

Heart valve incompetency is a serious problem. For example, heart disease can cause the chambers of the heart to expand and weaken. With specific reference to the mitral valve, as a result of aging or disease, the left ventricle dilates, and the papillary muscles are displaced. Consequently, the annulus of the mitral valve dilates excessively. In this state of dilation, valve leaflets may no longer effectively close, or coapt, during systolic contraction. Consequently, regurgitation (or retrograde flow back across the valve that should be closed) of blood occurs during ventricular contraction, and cardiac output is decreased.

This condition may be addressed by the surgical implantation of an implant. This procedure is performed open chest and is time consuming. In open heart surgery, the patient is put on cardiopulmonary bypass with its associated risks of morbidity and mortality due to stroke, thrombosis, heart attack and extended recovery time. Improvements in this field are therefore desirable.

SUMMARY

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices and methods for delivery of cardiac implants.

The following disclosure describes non-limiting examples of some embodiments. For instance, other embodiments of the disclosed systems and methods may or may not include the features described herein. Moreover, disclosed advantages and benefits can apply only to certain embodiments and should not be used to limit the disclosure.

A deployment restraint is described that may be used with various implants delivered via transcatheter delivery to address heart valve incompetency. For example, heart disease can cause the chambers of the heart to expand and weaken. With specific reference to the mitral valve, as a result of aging or disease, the left ventricle dilates, and the papillary muscles are displaced. Consequently, the annulus of the mitral valve dilates excessively. In this state of dilation, valve leaflets no longer effectively close, or coapt, during systolic contraction. Consequently, regurgitation (or retrograde flow back across the valve that should be closed) of blood occurs during ventricular contraction and cardiac output is decreased. The implant may be delivered in a delivery configuration via transcatheter delivery and deployed and expanded within the heart. The implant engages tissue surrounding the valve annulus and contracts to reshape, e.g. decrease the width of, the annulus. Transcatheter delivery may reduce the duration of the procedure and, more particularly, the duration that the patient is on bypass. Furthermore, it should be recognized that the implant can be deployed to treat mitral or tricuspid valve regurgitation.

The deployment restraint described in various embodiments herein may be used with such implants. In one embodiment, the restraint may include a distal substantially cylindrically-shaped section and an elongated shaft connected to the distal section for longitudinally advancing the distal section through the implant. The distal, substantially cylindrically-shaped section of the restraint may include a series of circumferential engagements for securing inwardly corresponding components of the implant. The restraint may be positioned to provide a radially inward force on the components of the implant, pulling in the implant to reduce the cross-section diameter to thereby reduce the cross-sectional deployment diameter of the implant. In one embodiment, the restraint may include a center shaft having a series of grooves configured to cooperate with corresponding splines of the implant. Distal or proximal advance of the restraint disengages the restraint from the implant. The implant may include a tubular frame configured to contract and be secured by the restraint in a contracted configuration and to expand upon disengagement from the restraint. The restraint may provide for a smaller overall cross-sectional profile of a transcatheter delivery system, for instance by negating the need for a distal delivery sheath.

According to one aspect, a central restraint includes a distal section including a substantially cylindrically-shape and including one or more grooves configured to releasably couple one or more splines disposed on an internal surface of an implant, and an elongated shaft connected to the distal section of the central restraint.

According to another aspect, a delivery system includes an implant having a distal end and a proximal end, the implant having a collapsed configuration and an expanded configuration and a central restraint including a distal section and an elongated shaft connected to the distal section of the central restraint, the distal section including a substantially cylindrically-shape and including one or more grooves configured to releasably couple one or more splines disposed on an internal surface of an implant. The one or more grooves and the one or more splines cooperate to retain the implant in the collapsed configuration during delivery to a treatment site.

According to a further aspect, a method of delivering an implant to a treatment site includes the steps of deploying an implant to a treatment site, the implant including a ring-shaped configuration and including a plurality of anchor housings disposed at a distal end, each anchor housing including a spline oriented towards an internal axis of the implant. The implant is deployed to the treatment site in a collapsed configuration where each spline of each anchor housing cooperates with one of a plurality of grooves of a distal section of a central restraint to retain the implant in the collapsed configuration. The method includes the step of axially translating the distal section of the central restraint proximally or distally to release each spline of each anchor housing from each groove of the distal section of the central restraint to release the implant from the collapsed configuration.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawing, can be arranged, substituted, combined, and designed in a wide variety of different configurations, all of which are explicitly contemplated and made part of this disclosure.

DETAILED DESCRIPTION

The following detailed description is directed to certain specific embodiments of the development. In this description, reference is made to the drawings wherein like parts or steps may be designated with like numerals throughout for clarity. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments necessarily mutually exclusive of other embodiments. Moreover, various features are described which may be exhibited by some embodiments and not by others. Similarly, various requirements are described which may be requirements for some embodiments but may not be requirements for other embodiments. Reference will now be made in detail to embodiments of the invention, examples of which are illustrated in the accompanying drawings. Wherever possible, the same reference numbers will be used throughout the drawings to refer to the same or like parts.

A cardiac implant may be delivered in a delivery configuration via transcatheter delivery and deployed and expanded within the heart. The implant may be a mechanical device capable of extending out to the dilated annulus of a heart valve, engaging the tissue of the heart valve annulus, and gathering it in to a smaller diameter. The implant may be delivered approximate and above the cardiac valve (tricuspid or mitral) annulus and subsequently implanted in the annular cardiac tissue just above the plane of the valve orifice.

Figure 1:
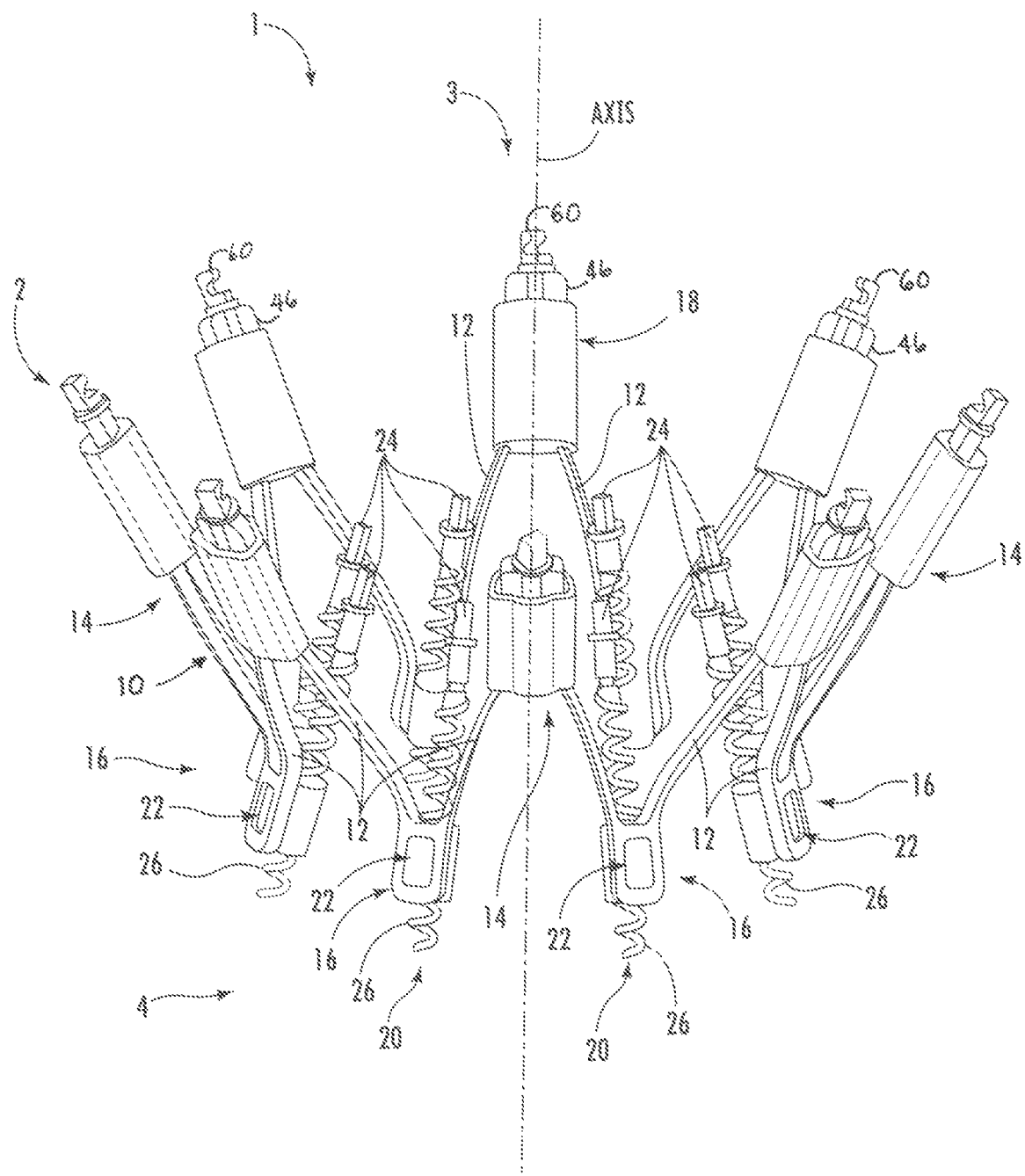
FIG. 1 is a perspective view of an embodiment of an implant which may be deployed using the integrated central restraint disclosed herein.

FIG. 1 is a perspective view of such an implant 1. The implant 1 is intended to be delivered proximate to, above and/or or within, the cardiac valve annulus. Unless otherwise stated, "valve" as used herein may refer to any of a variety of valves, including the tricuspid or mitral valve of the heart. The implant 1 may be subsequently implanted in the annular cardiac tissue just above the plane of the valve orifice. In some embodiments, the implant may be a heart valve replacement including valve leaflets, which can be implanted in annular cardiac tissue and extend into the valve annulus, as further described herein.

With reference to FIG. 1, the implant 1 is an implantable device. The implant 1 forms a lumen or opening 3 extending through the implant 1. For sake of description, a geometric reference longitudinal axis is indicated. The implant 1 may be described with reference to the axis. An "axial" direction refers to movement generally parallel to the axis in either an upward or downward direction, unless otherwise indicated. The opening 3 extends axially between an upper portion 2 of the implant 1 and a lower portion 4 of the implant 1. The upper and lower portions 2, 4 may include various features of the implant 1. The terms "upper," "upward," and the like refer to directions generally toward the upper portion or proximal end 2, and the terms "lower," "downward," and the like refer to directions generally toward the lower portion or distal end 4, unless otherwise indicated. "Proximal" refers to a direction in the upward direction, and "distal" refers to a direction in the downward direction. The terms "inner," "inward," and the like refer to directions generally toward the axis, and terms "outer," "outward," and the like refer to directions generally away from the axis. These geometric references generally apply unless otherwise indicated, either explicitly or by context.

The implant 1 includes a frame 10. The frame 10 extends circumferentially around and partially axially along the axis. The axis may be defined by the frame 10. The frame 10 is generally symmetric with respect to the axis. However, the frame 10 need not be symmetric with respect to the axis. The frame 10 has a generally tubular shape. "Tubular" includes circular as well as other rounded or otherwise closed shapes. The frame 10 is generally circular about the axis. The frame 10 may be circular, rounded, ellipsoidal, segmented, other shapes, or combinations thereof. The frame 10 may change shape, size, configuration, etc. The frame 10 may have various shapes, sizes, configurations etc. at various phases of use, e.g. pre-delivery, during delivery, after engagement with tissue, after contracting the annulus, post-contraction, during the lifetime of use while implanted, etc.

The implant 1 includes one or more struts 12. To simplify the figure, only a subset of like components in FIG. 1 are numbered. The struts 12 may form all or part of the frame 10. The struts 12 are elongated structural members. The struts 12 and/or other parts of the frame 10 are formed of a metal alloy. The struts 12 and/or other parts of the frame 10 may be formed of an alloy of nickel titanium. In some embodiments, the struts 12 and/or other parts of the frame 10 are formed of other metals, metal alloys, plastics, polymers, composites, other suitable materials, or combinations thereof. There are sixteen struts 12. In some embodiments, there may be fewer or more than sixteen struts 12. In some embodiments, there may be at least two, four, six, eight, ten, twelve, fourteen, eighteen, twenty, twenty-two, twenty-four, twenty-six, twenty-eight, thirty, or more struts 12.

The struts 12 may be part of the same, monolithic piece of material (e.g. tube stock). Thus, the struts 12 may refer to different portions of the same, extensive component. The struts 12 may be formed from the same piece of material. The struts 12 may be formed separately and attached permanently together, e.g. by welding, etc. In some embodiments, the struts 12 may be separate components that are detachably coupled together by other components of the implant 1. For example, the struts 12 may be held together via various components described herein, such as collars 18, anchors 20, other features, or combinations thereof. In some embodiments, separate strut units may include two or more struts permanently attached together such as at an apex, and the separate units may each be coupled together, either permanently or detachably, to form the frame 10. In some embodiments, the struts 12 may be attached by hinges, pins, or other suitable means.

The elongated, middle portions of the struts 12 have a generally rectangular cross-section but can vary in circumferential width and radial thickness to allow for different beam characteristics and forces applied as the collars are advanced. This may facilitate for example post implantation constriction or remodeling of the annulus, as further described. The long ends of the rectangular cross-section of the struts 12 extend along the circumference of the frame 10. "Circumference" as used herein generally refers to a perimeter or boundary and can refer to a circular or other rounded or non-rounded path lying in a plane substantially transverse to the axis, unless otherwise stated. The short ends of the rectangular cross-section of the struts 12 extend transversely to the circumference of the frame 10. In some embodiments, other configurations and/or cross-sectional shapes of the struts 12 may be implemented. The cross-section may be rounded, circular, other shapes, or combinations thereof.

The struts 12 extend around the axis to form the various shapes of the frame 10. The struts 12 are arranged such that the wall pattern of the frame 10 may be approximately sinusoidally or zig-zag shaped. In some embodiments, the wall pattern may have other suitable shapes, sinusoidal or otherwise. The vertices of the sinusoidal shaped frame 10 may be pointed or rounded.

Pairs of adjacent struts 12 meet at an apex. At least a first pair of adjacent struts 12 meets at an upper apex or crown 14 at the upper portion 2 of the implant 1. At least a second pair of adjacent struts 12 meets at a lower apex or crown 16 at the lower portion 4 of the implant 1. The terms "apex," apices," and the like may be used interchangeably with terms "crown," "crowns," and the like, as used herein and as used in any reference incorporated by reference herein, unless otherwise stated. The upper and lower crowns 14, 16 are spaced sequentially along the circumference of the frame 10, with one of the upper crowns 14 followed by one of the lower crowns 16, followed by another one of the upper crowns 14, etc. In the illustrated embodiment, there are eight upper crowns 14 and eight lower crowns 16. In some embodiments, there may be no more than about six or four or fewer or more than eight or ten or twelve upper and lower crowns 14, 16, depending on the number of struts 12 and the resulting number of apices.

The upper crowns 14 are each configured to have a restraint such as a collar 18 fitted over and/or around the upper crown 14. Thus, the upper crowns 14 may include various features, dimensions, etc. as described herein for coupling with the collar 18, as further described. The upper crowns 14 are shown partially covered by the collars 18 in FIG. 1. In some embodiments, one or more of the upper crowns 14 may not have the collar 18. In some embodiments, fewer than all of the upper crowns 14 are configured to receive the collar 18. In some embodiments, all of the upper crowns 14 may be configured to receive the collar 18 but when implanted only some of the upper crowns 14 may actually include the collar 18.

The proximal end 2 of the implant 1 includes the shafts 46 with proximal couplings 60 and collars 18 surrounding pairs of adjacent struts 12. Rotation of the shafts 46 using couplings 60 axially translates the collars 18 along the struts 12, thereby modifying the circumference of the frame 10.

The distal end 4 of implant 1 is shown to include anchor assemblies each having an anchor housing 22 and an embodiment of the anchor 20 having a distal helical portion 26 with a proximal coupling 24. The housing 22 is coupled with the distal apexes 16 and receives the anchors 20 therethrough. Rotation of the proximal couplings 24 by driver tubes which extend up through a delivery catheter to a proximal handle (not shown) translates the distal helical portions 26 of the anchors 20 through the anchor housings 22. The proximal couplings 24 are advantageously independently controllable. The collars 18 and anchors 20 are shown in a relative proximal position and may be adjusted proximally or distally therefrom to effect various changes in the frame 10.

Figure 2:
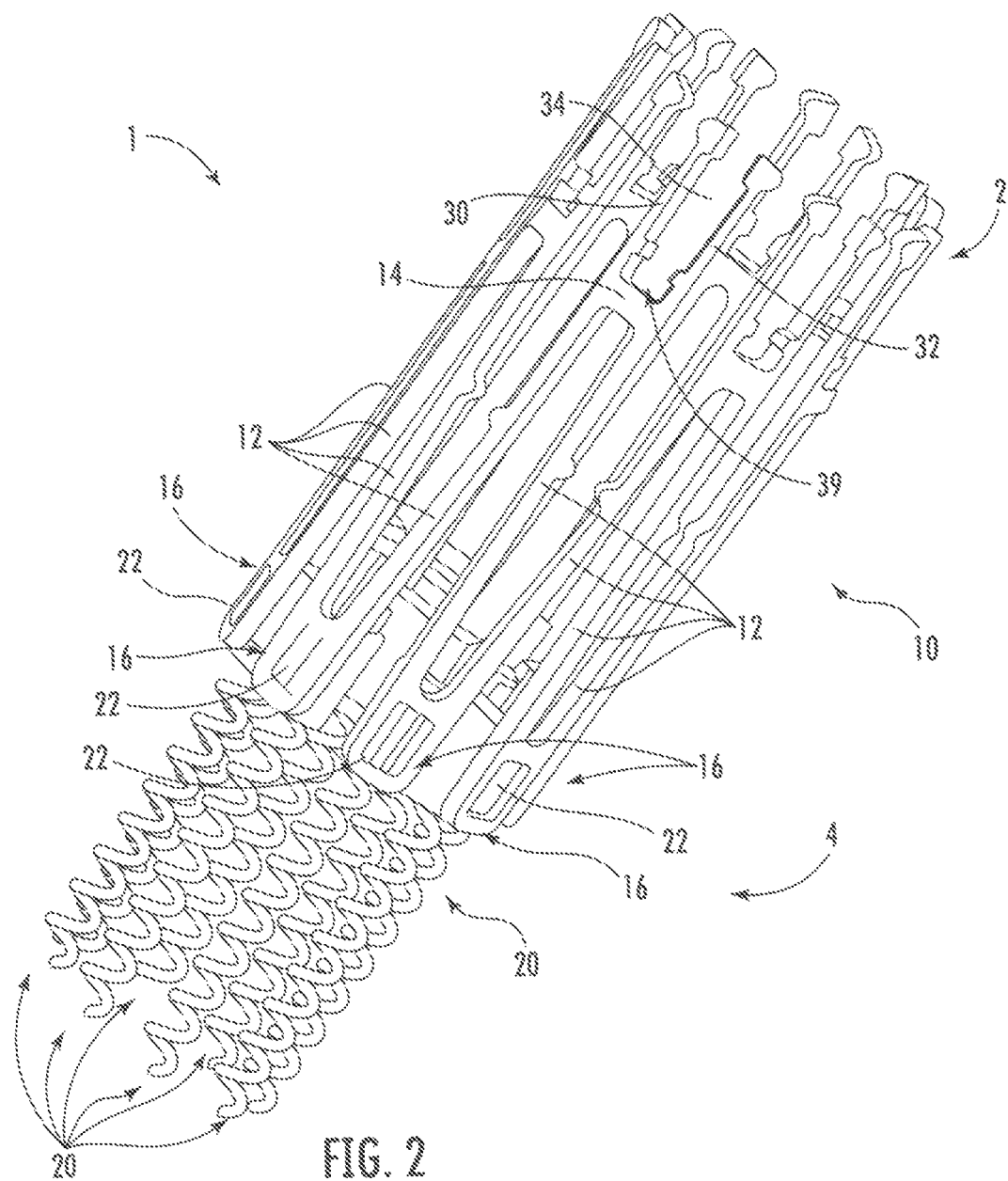
FIG. 2 is a perspective view of one embodiment of the implant of FIG. 1 in a compressed state with collars of the proximal apexes removed for purposes of illustration.

FIG. 2 is a perspective view of the implant 1 of FIG. 1 shown in a compressed configuration, for example a configuration suitable for delivery through a delivery catheter. In FIG. 2, the proximal end 2 of the implant is shown without the cinching or contracting mechanism described herein (threaded shaft 46, collar 18, etc. of FIG. 1) for ease of illustration. The frame 10 may include struts 12 forming proximal apexes 14 and distal apexes 16, first and second proximal supports 30, 32 forming windows 34 and window 39 which may be used to support a threaded shaft 46 within the collar 18 (shown in FIG. 1), allowing for free rotation of the threaded shaft 46 within the frame 10 and enabling the collar 18 to translate axially along the threaded shaft 46 to cinch the frame 10. As described in further detail above, the struts 12 may be joined at the proximal and distal apexes 14, 16 and the frame 10 may be formed of a metal alloy, such as an alloy of nickel titanium.

The distal end 4 of the implant 1 supports a plurality of anchor assemblies comprised of anchor housings 22 and anchors 20. Although the anchors 20 are shown extending distally through the anchor housings 22 in FIG. 2, during delivery the anchors 20 are advantageously disposed within the central axis of the implant 1.

As mentioned, an anchor assembly may include an anchor housing 22 and an anchor 20. The anchor housing 22 is coupled with, for example attached to, the distal end 4 of the implant 1. As shown, the housing 22 is attached to the frame 10 at the distal apex 16. The housing 22 may be a separate part that is attached to the frame 10, or the housing 22 may be integral with the frame 10, such as with the distal apex 16. In some embodiments, the anchor housing may be snap fit into a cutout of the distal apex 16. The housings 22 are shown located primarily on a radially inward side of the distal apexes 16. The housing 22 may be located entirely on a radially inward side. The housings 22 extend from the apex 16 toward the central longitudinal axis of the implant 1 (shown, for example, in FIG. 1).

In the configuration of FIG. 2, a sheath (not shown) may surround the delivery catheter extending past the delivery catheter's distal end. The implant 1 may be compressed and retained in its compressed condition (as shown in FIG. 2) by the sheath for delivery to the valve treatment site. When the sheath is withdrawn, the implant 1 returns to its expanded diameter (as shown in FIG. 1) to engage the dilated annulus. Anchors 20 may then be advanced through the anchor housings 22 to penetrate the tissue of the heart valve annulus. The implant may then be forcibly reduced in size, for example by advancing collars over struts as described. This reconfigures the valve annulus down to a smaller diameter, reducing and/or eliminating the regurgitation.

In practice, the combination of a delivery system, sheath and guide catheter may present a relatively larger profile with respect to the patient anatomy to which it must traverse. It would be preferable to reduce the profile of the overall system. This is especially helpful for transcatheter delivery methods and systems. The integrated central restraint mechanism disclosed herein eliminates the need for the surrounding sheath, reducing the size of the overall system. The central restraint for use with the various ring-like implants will now be described.

Figure 3:
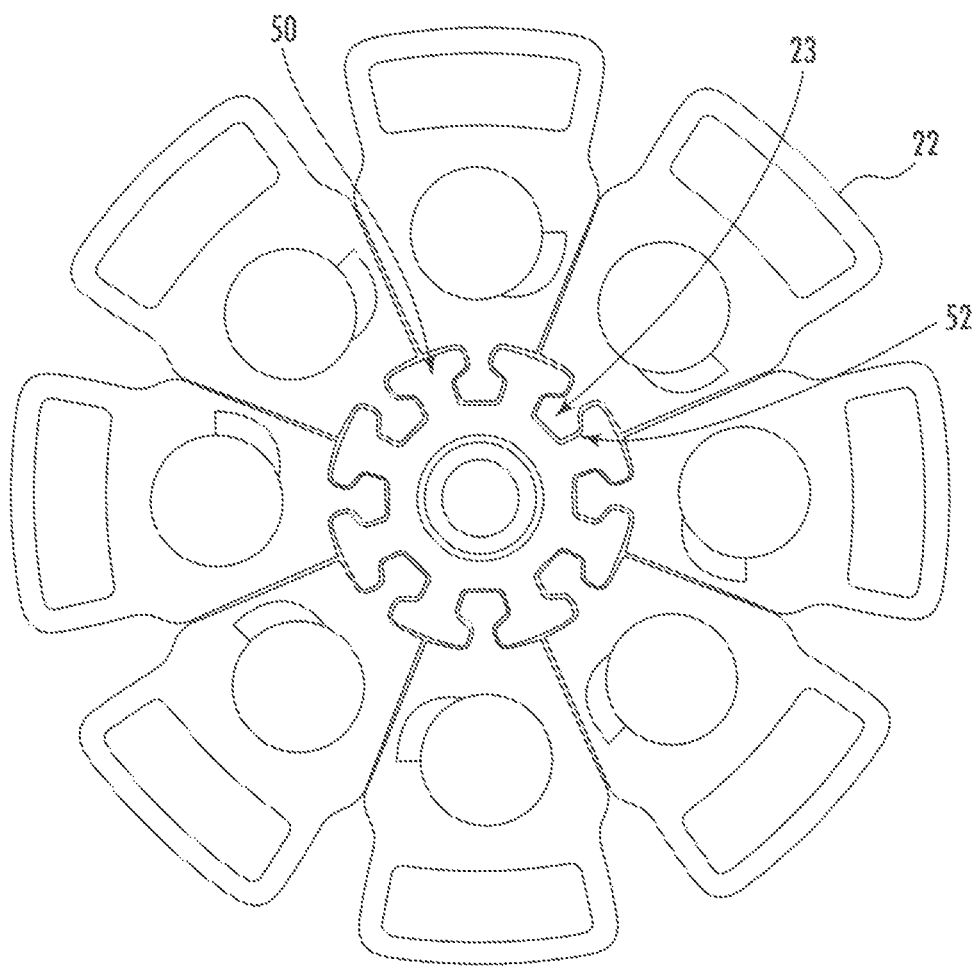
FIG. 3 is a proximally facing view of the central restraint mechanism in engagement with the anchor housings of an exemplary implantable device.
Figure 4:
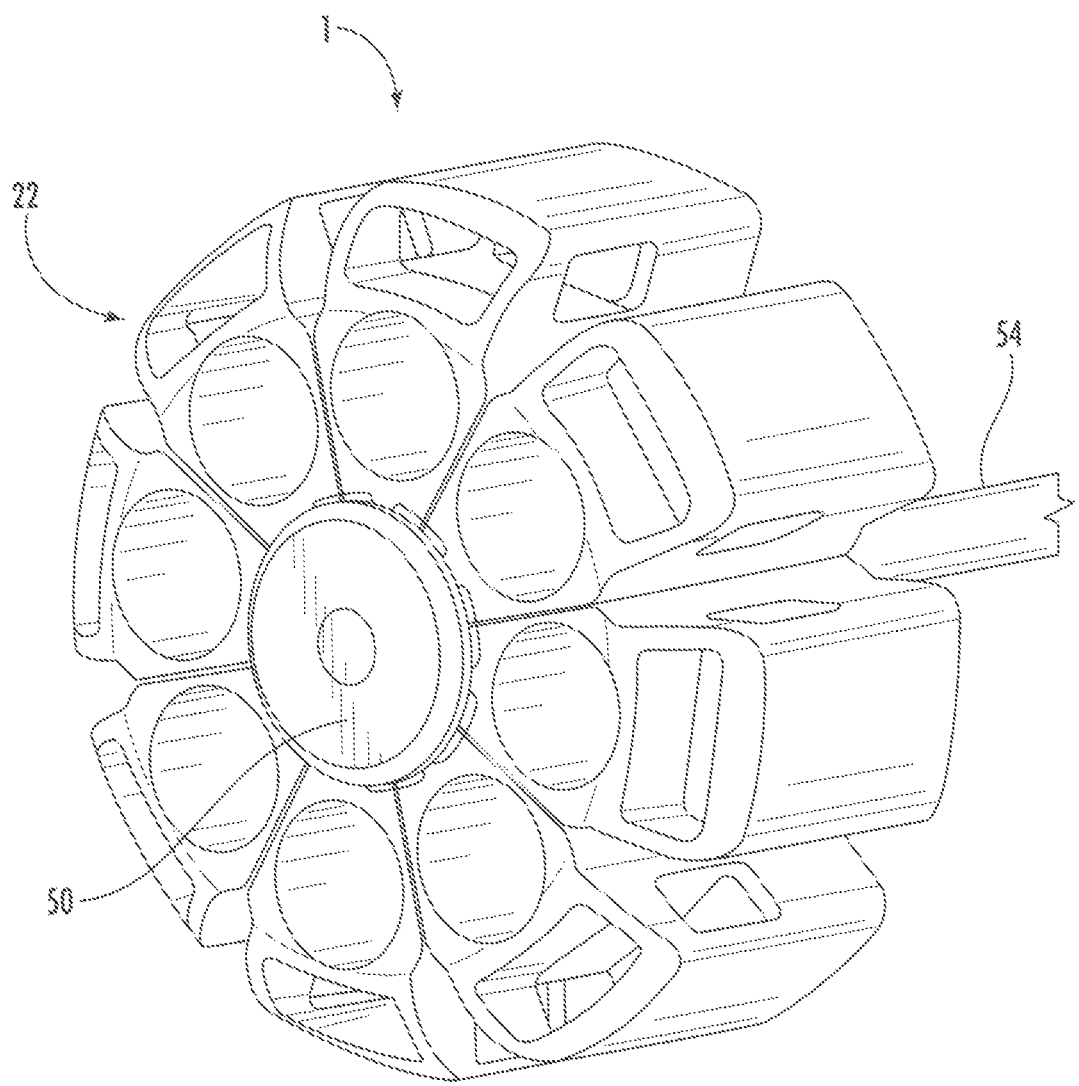
FIG. 4 is a side perspective view of the central restraint mechanism engaged with the anchor housings for delivery of the implantable device.

FIGS. 3 and 4 illustrate perspective views of an implantable device such as implant 1 in a collapsed and restrained configuration, for example constrained with a retention device 50 as disclosed herein, for delivery proximate a cardiac valve. For purposes of simplicity, only the anchor housings 22 are shown. FIG. 3 is a proximally facing end view of the implant 1, wherein the anchor housings 22 are shown held tightly together by the central restraining mechanism 50.

Each anchor housing 22 includes a spline 23 running longitudinally along the length of its internal diameter. The splines cooperate with a series of grooves 52 running longitudinally along an external surface of the central restraining mechanism, with each groove 52 configured to accept a spline 23 of an anchor housing 22. To load the implant for delivery, while the implantable device and its anchor assemblies 22 are held in the compressed configuration, central restraining mechanism 50 may be advanced through the central axis of the implantable device such that grooves 52 are aligned with and accept splines 23, which translate through the grooves to the distal end of the implant, thereby restraining anchor housings 22A, and thus the implant, in the compressed configuration for delivery through the guide catheter to the treatment site.

FIG. 4 is a side view perspective of a portion of an implant 1, including anchor housings 22 retained by a central retaining mechanism 50. A rod 54, shown extending through the central axis of the implant 1, is coupled to or integral with the central retaining mechanism 50 and extends proximally from the implant 1 to a control handle. The rod 54 may be manipulated to release the central retaining mechanism 50 from the anchor housings 22, as described below with regard to FIG. 5

Figure 5:
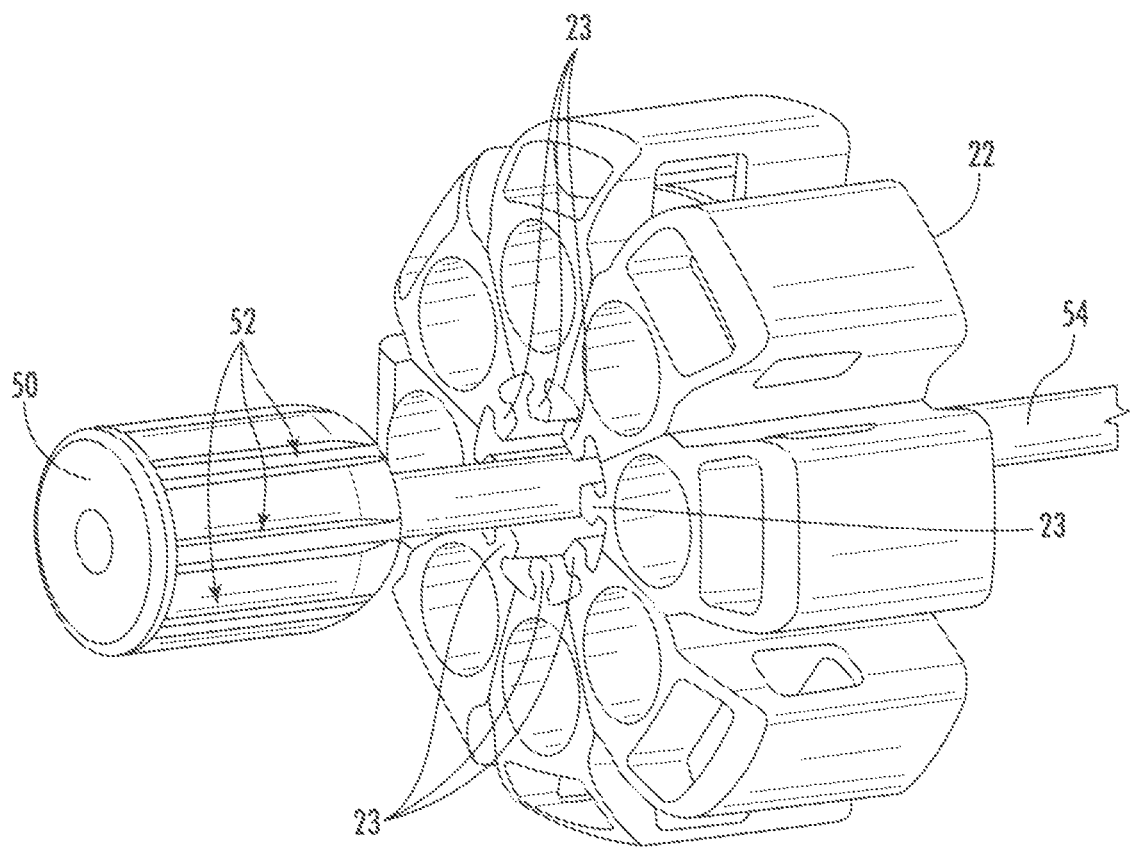
FIG. 5 is a perspective view of the restraint mechanism advanced distally out of engagement with the anchor housings.

When delivered proximate the target cardiac valve, central restraint mechanism 50 may be advanced distally by movement of connecting rod 54, such as depicted in FIG. 5. During distal advancement of the central restraint mechanism, the implant 1 is held in place by drivers and other connectors between the implant 1 and the delivery catheter. As a result, the splines 23 of the anchor housings 22 slide through the grooves 52 of the central restraint mechanism.

Figure 6:
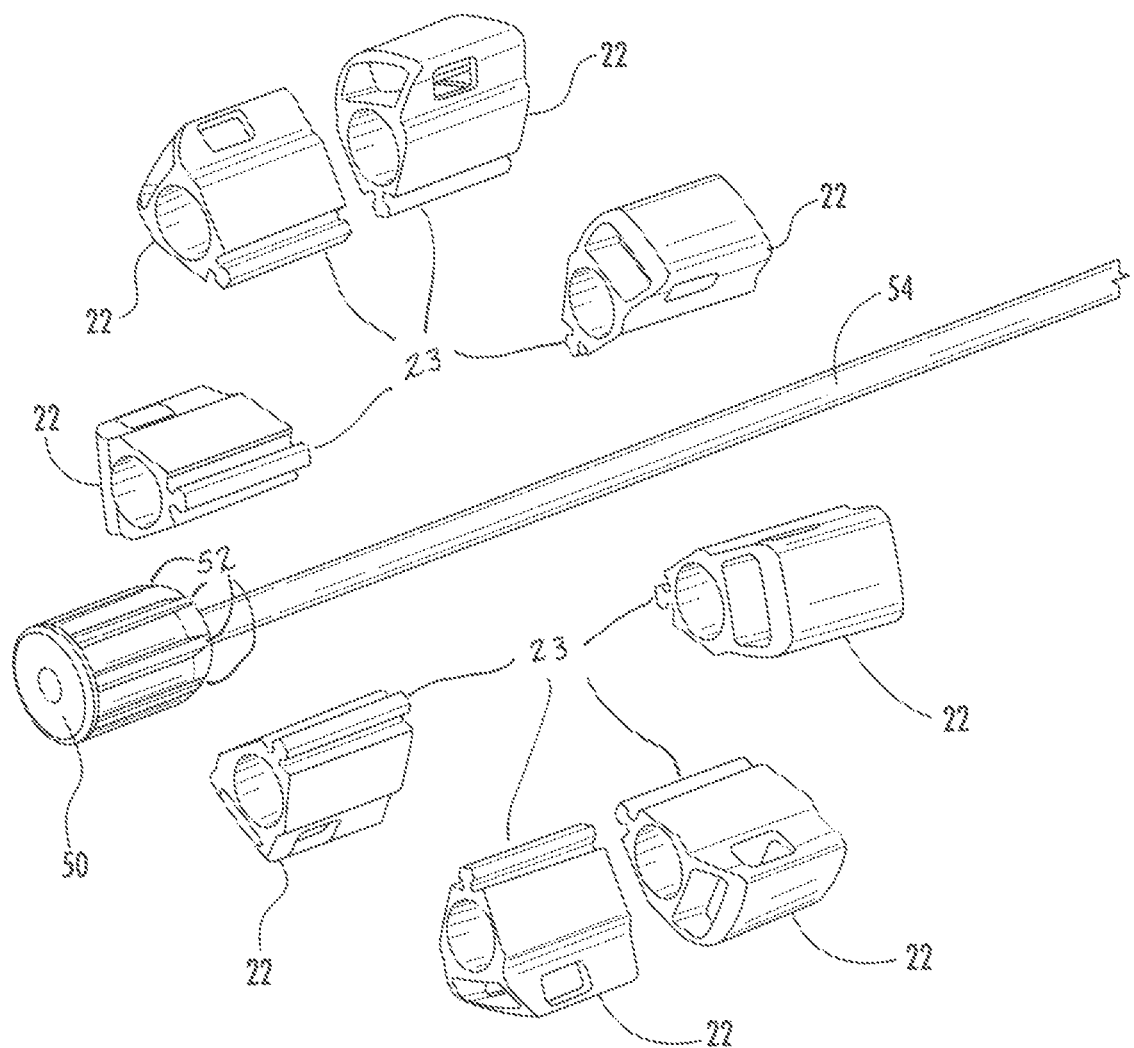
FIG. 6 illustrates the restraint mechanism advanced distally, as in FIG. 5, with the implantable device and its anchor housings assuming their expanded, free state.

Once central restraint mechanism 50 is advanced such that grooves 52 clear engagement with anchor housing splines 23, the implantable device and its anchor housings 22 may revert to its free state of non-constrained configuration. For example, as shown in FIG. 6, the splines 23 have been released from the grooves 52, allowing the anchor housings 22 of the implant 1 to expand, taking a shape such as that generally shown in FIG. 1. For purposes of simplicity, all components of the implant 1 are not shown in FIG. 6.

The use of a central restraining mechanism allows the implant to be retained in a constrained configuration without the use of an outer sheath. Historically, an outer sheath could be used to restrain the implantable device for advancement and delivery to the target heart valve. Due to the presence of this outer sheath, a 33 French guide catheter was needed to accommodate the implantable device, its delivery system, and the outer sheath. Central restraint mechanism 50 restrains the implantable device and its anchor assemblies 22 without the need for this outer sheath. As such, for example, a 28 French guide catheter can now be used to advance the delivery catheter and implantable device. The central restraint mechanism has, therefore, significantly reduced the overall diameter of the catheter by greater than 15%.

Figure 7A:
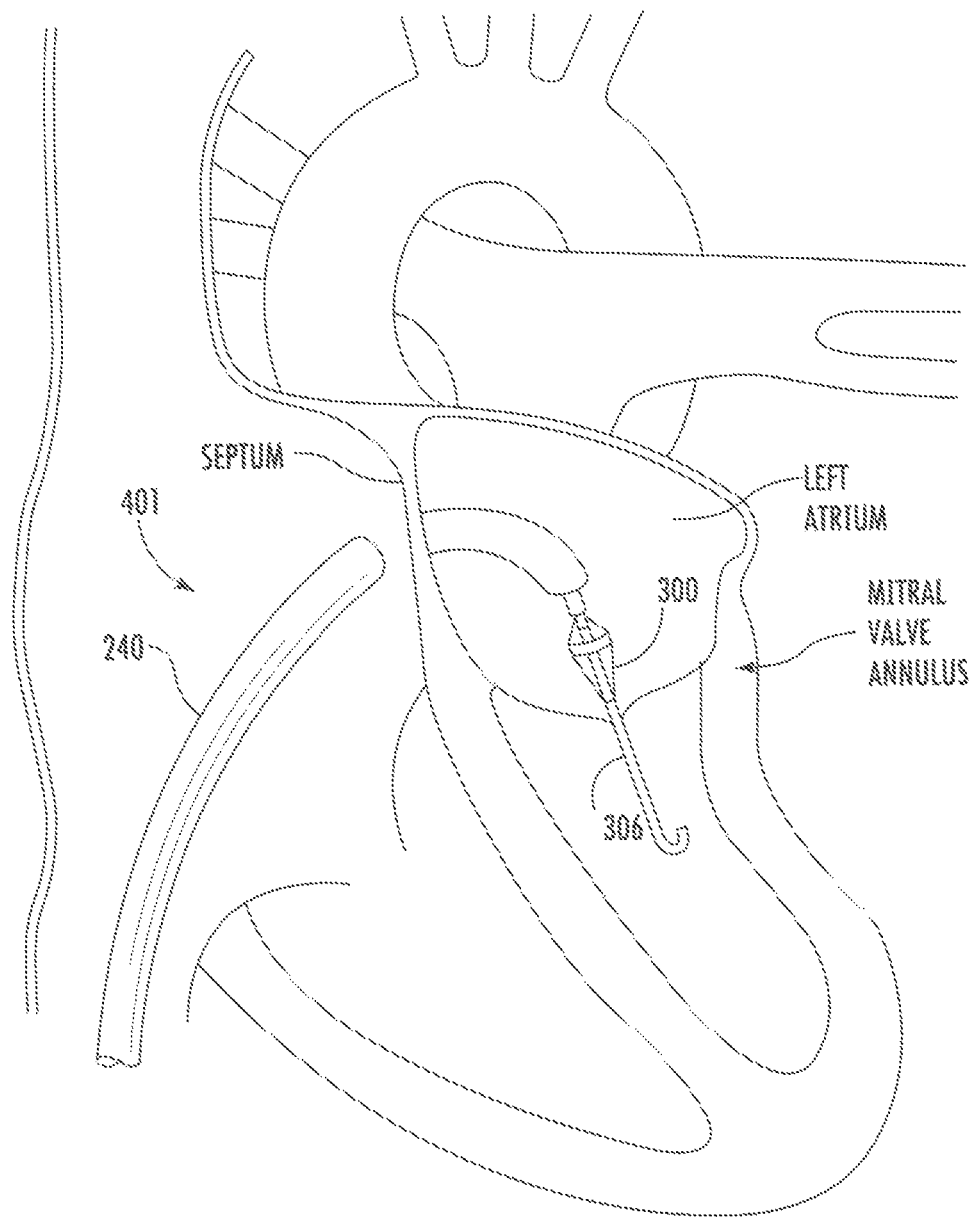
FIGS. 7A and 7B are sequential perspective views of an embodiment of a delivery system with imaging capability showing an embodiment of a method for the delivery, positioning and anchoring of the various implants that may use embodiments of the restraint described herein.
Figure 7B:
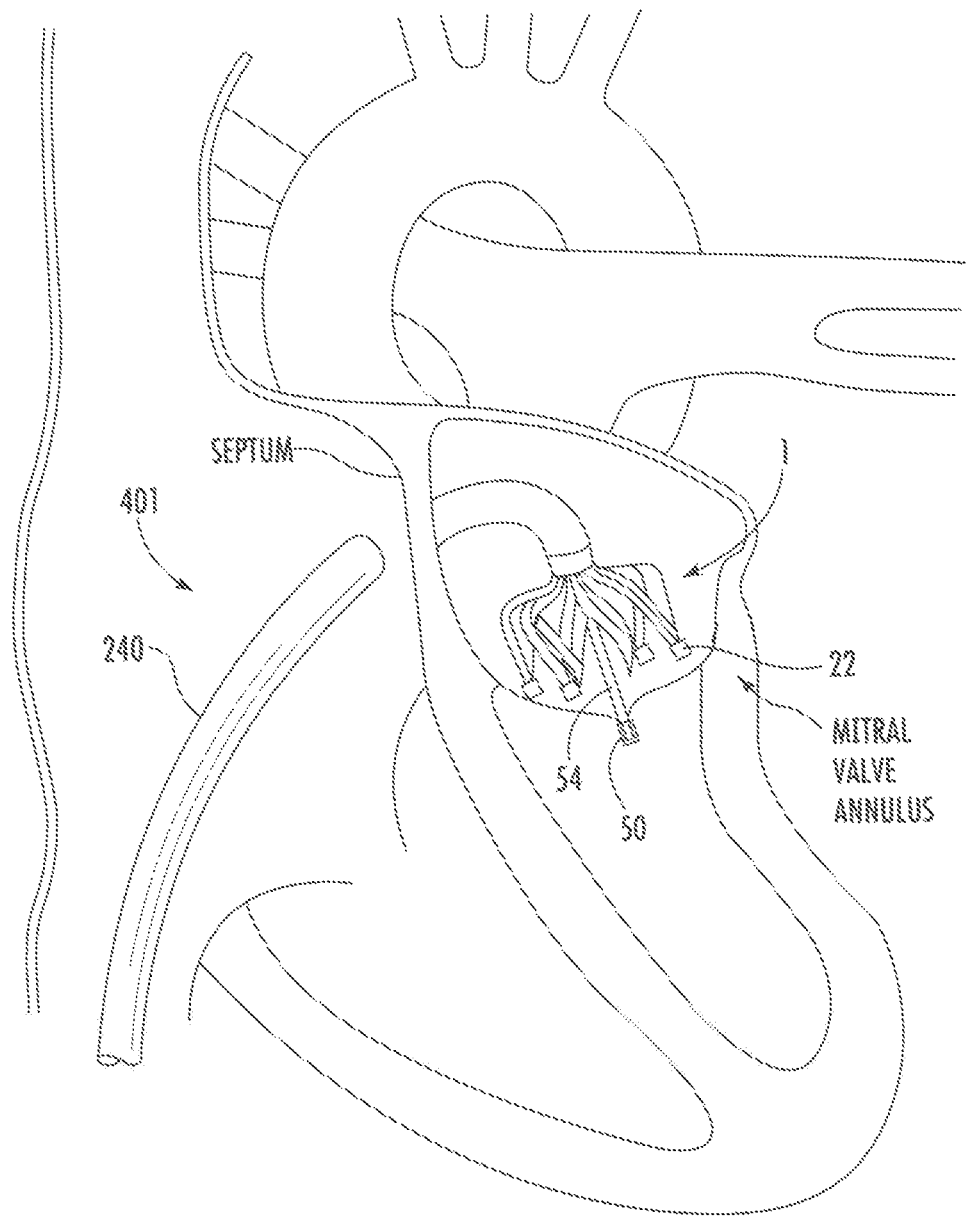

FIGS. 7A, 7B illustrate exemplary steps that may be performed in a method to deliver an implant including a central restraining mechanism which, for example, enables the implant to be delivered in a more tightly compressed configuration, allowing the use of a smaller diameter guide catheter in place of a delivery catheter and guide catheter combination. FIGS. 7A and 7B illustrate an embodiment of a delivery system 401 which may be used to position an implant to reshape the valve annulus. The implant may be inserted using the delivery system 401 via access to the vasculature of the leg, in particular the femoral vein or the iliac vein. The implant in FIG. 7A may be loaded in the guide catheter 240 in a compressed state and secured in the compressed state using the restraint mechanism as described with regard to FIG. 2.

As shown in FIG. 7A, the system 401 includes a guide catheter 240 that may be advanced across the septum separating the upper chambers of the heart, although the disclosure is not limited to use with a particular delivery pathway. In some embodiments, the guide catheter may include an ICE catheter 300 for use in visualizing navigation of a guidewire 306 to a position above the heart valve annulus, for example, the mitral valve annulus, as shown, although other visualization techniques may alternatively be used. When the distal end of the guide catheter is positioned, the implant may be released from the distal end of the delivery system 401 above and proximate to the mitral valve annulus. During the release, the push rod 54 may be advanced through the central axis of the implant 1, releasing the anchor housings 22 and allowing the implant 1 to expand as shown in FIG. 7B. The central restrain may then be withdrawn proximally through the catheter and away from the treatment site. Anchors may then be advanced through the anchor housings 22 toward the mitral valve annulus tissue above the mitral valve leaflets. It should also be understood that treatment of the tricuspid valve could involve insertion of the system 401 for access through the jugular vein whereby the system is then advanced down the superior vena cava and into the right atrium proximate and above the tricuspid valve annulus.

Various modifications to the implementations described in this disclosure will be readily apparent to those skilled in the art, and the generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations, unless otherwise stated.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. Additionally, other implementations are within the scope of the following claims. In some cases, the actions recited in the claims can be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A central restraint comprising:
   a distal section comprising a substantially cylindrical shape and including a plurality of longitudinally-extending grooves on an outer surface thereof having open longitudinal ends configured to be releasably axially-slidably engaged with a respective radially-inwardly and longitudinally extending spline formed on an internal surface of an implant; and
   an elongated shaft connected to the distal section of the central restraint.

2. The central restraint of claim 1, wherein the plurality of grooves are radially spaced apart along an exterior circumference of the distal section of the central restraint.

3. The central restraint of claim 2, wherein the plurality of grooves are longitudinally disposed upon the exterior circumference of the distal section of the central restraint.

4. The central restraint of claim 3, wherein the elongate shaft is configured to axially translate the distal section of the central restraint relative to the implant.

5. The central restraint of claim 3, wherein the plurality of grooves cooperate with a respective one of a plurality of splines of the implant to retain the implant in a collapsed configuration.

6. A delivery system for an implantable cardiac device, the system comprising:
   an implant having a distal end and a proximal end and one or more longitudinally-extending splines disposed on an internal surface of the implant between the distal end and the proximal end, wherein the implant is shiftable between a collapsed configuration and an expanded configuration; and
   a central restraint having a plurality of grooves extending longitudinally along the exterior of the central restraint and spaced apart from one another, each of the plurality of longitudinally-extending grooves configured to axially-slidingly receive a spline on the internal surface of the implant to hold the implant in the collapsed configuration.

7. The delivery system of claim 6, wherein the central restraint further comprises:
   a distal section comprising a substantially cylindrical shape configured to be longitudinally inserted into an interior of the implant along a central axis of the implant; and
   an elongated shaft connected to the distal section of the central restraint.

8. The delivery system of claim 7, wherein the plurality of longitudinally-extending grooves are disposed upon and circumferentially spaced apart along a portion of an exterior circumference of the distal section of the central restraint.

9. The delivery system of claim 8, wherein at least one of the one or more splines extends radially inwardly from the inner surface of the implant and is configured to slide longitudinally into an open longitudinal end of one of the plurality of grooves.

10. The delivery system of claim 7, wherein the elongate shaft is configured to axially translate the distal section of the central restraint relative to the implant.

11. The delivery system of claim 6, wherein the one or more grooves cooperate with the one or more splines of the implant to retain the implant in a collapsed configuration.

12. The delivery system of claim 6, wherein axial translation of the elongated shaft within the implant releases the splines from the grooves to expand the implant to the expanded configuration.

13. The delivery system of claim 12, wherein axial translation includes one of a proximal translation or a distal translation.

14. The delivery system of claim 13, wherein:
   the implant comprises a plurality of anchor assemblies, each anchor assembly having an anchor housing, each anchor housing having an internal surface, and each anchor housing coupled with a lower crown; and
   at least one of the one or more splines of the implant is disposed on an internal surface of at least one of the anchor housings.

15. The delivery system of claim 14, wherein each spline extends longitudinally along an associated anchor housing.

16. The delivery system of claim 15, wherein each spline extends radially inward towards a central axis of the implant.

17. The delivery system of claim 14, wherein:
   the implant comprises a ring-like member having upper crowns, lower crowns, and struts between the upper crowns and the lower crowns; and
   each anchor housing is snap fit into a cut out in a corresponding lower crown.

18. A method of delivering an implant to a treatment site, the method comprising:
   deploying an implant to a treatment site, the implant comprising one or more longitudinally-extending splines disposed on an internal surface of the implant and oriented towards an internal axis of the implant, wherein the implant is deployed to the treatment site by being advanced distally toward the treatment site in a collapsed configuration with at least one spline cooperating with a corresponding one of a plurality of longitudinally-extending grooves on an exterior surface of a central restraint to retain the implant in the collapsed configuration; and
   axially translating the central restraint with respect to the implant to cause the at least one spline to move out of an axial end of the corresponding longitudinally-extending groove of the central restraint to release the implant from the collapsed configuration to an expanded configuration.

19. The method of claim 18 further comprising withdrawing the central restraint through the implant in the expanded configuration.

20. The delivery system of claim 6, wherein:
   the splines are formed on the internal surface of the implant extending longitudinally therealong and projecting radially inwardly towards a central axis of the implant; and
   the grooves on the central restraint axially slidingly receive the splines when the implant is held in a constrained configuration.

* * * * *